US012761720B2

(12) United States Patent
Kayama et al.

(10) Patent No.: US 12,761,720 B2
(45) Date of Patent: Oct. 13, 2026

(54) CONTENT PLAYBACK DEVICE, CONTENT PLAYBACK METHOD, AND PROGRAM

(71) Applicant: LIFE QUEST INC., Tokyo (JP)

(72) Inventors: Tetsu Kayama, Tokyo (JP); Ryozo Saito, Tokyo (JP); Yasuhide Yoshihara, Kyoto (JP)

(73) Assignee: LIFE QUEST INC., Tokyo (JP)

( * ) Notice: Subject to any disclaimer, the term of this patent is extended or adjusted under 35 U.S.C. 154(b) by 290 days.

(21) Appl. No.: 17/759,752

(22) PCT Filed: Feb. 7, 2020

(86) PCT No.: PCT/JP2020/005006

§ 371 (c)(1),
(2) Date: Jul. 29, 2022

(87) PCT Pub. No.: WO2021/157099

PCT Pub. Date: Aug. 12, 2021

(65) Prior Publication Data

US 2023/0118151 A1 Apr. 20, 2023

(51) Int. Cl.
*G06F 3/01* (2006.01)
*A61B 5/16* (2006.01)
(Continued)

(52) U.S. Cl.
CPC .............. *G06F 3/011* (2013.01); *A61B 5/165* (2013.01); *A61B 5/374* (2021.01); *A61M 21/00* (2013.01);
(Continued)

(58) Field of Classification Search
None
See application file for complete search history.

(56) References Cited

U.S. PATENT DOCUMENTS

| | | | |
|---|---|---|---|
| 5,772,508 | A | 6/1998 | Sugita et al. |
| 2007/0123350 | A1 | 5/2007 | Soderlund |

(Continued)

FOREIGN PATENT DOCUMENTS

| | | | |
|---|---|---|---|
| CN | 105844072 | A | 8/2016 |
| CN | 108512995 | A | 9/2018 |

(Continued)

OTHER PUBLICATIONS

EESR/EPO, The extended European search report issued on Jan. 3, 2023 in European Patent Application No. 20917283.2, 11 pages.

(Continued)

*Primary Examiner* — Kevin Y Kim
(74) *Attorney, Agent, or Firm* — MASUVALLEY & PARTNERS; Peter Martinez

(57) ABSTRACT

The present invention improves interest in content. A main body device (2) includes a biological information acquisition device (7) for acquiring biological information of a player and a CPU (81). The CPU (81) sets, to a psychological state flag, a psychological state corresponding to a situation of a game during play as a targeted psychological state. Then, the CPU (81) specifies the psychological state of the player from the biological information acquired by the biological information acquisition device (7). In addition, the CPU (81) changes a mode of the game so that the psychological state specified from the biological information matches the targeted psychological state.

7 Claims, 9 Drawing Sheets

(51) Int. Cl.

| | |
|---|---|
| ***A61B 5/374*** | (2021.01) |
| ***A61M 21/00*** | (2006.01) |
| ***A63F 13/212*** | (2014.01) |
| ***A63F 13/60*** | (2014.01) |

(52) U.S. Cl.
CPC ............ *A63F 13/212* (2014.09); *A63F 13/60* (2014.09); *G06F 3/015* (2013.01); *A61M 2021/0027* (2013.01); *A61M 2021/005* (2013.01); *G06F 2203/011* (2013.01)

(56) References Cited

U.S. PATENT DOCUMENTS

| | | | | |
|---|---|---|---|---|
| 2014/0167968 | A1 | 6/2014 | Tuzsuzov | |
| 2015/0245156 | A1* | 8/2015 | Tsang | H04R 3/00 381/61 |
| 2017/0007165 | A1 | 1/2017 | Jain et al. | |
| 2018/0279900 | A1* | 10/2018 | Moghaddam | A61B 5/0006 |
| 2020/0288986 | A1* | 9/2020 | Sato | A61B 5/0024 |

FOREIGN PATENT DOCUMENTS

| | | | |
|---|---|---|---|
| JP | H7-16349 | A | 1/1995 |
| JP | H7-124331 | A | 5/1995 |
| JP | H8-191955 | A | 7/1996 |
| JP | H9-22314 | A | 1/1997 |
| JP | H10-258183 | A | 9/1998 |
| JP | 2001252265 | A | 9/2001 |
| JP | 2007-130212 | A | 5/2007 |
| JP | 2007-517548 | A | 7/2007 |
| JP | 2013-258555 | A | 12/2013 |
| JP | 2014-515129 | A | 6/2014 |
| JP | 2018-201769 | A | 12/2018 |
| JP | 2019-082952 | A | 5/2019 |
| WO | WO201507634 | A1 | 1/2015 |

OTHER PUBLICATIONS

JPO, Decision to Grant mailed on Dec. 7, 2021 in Japanese Patent Applciation No. 2021-526710, 8 pages.

To JPO, Written Opinion, Reply to Office Action, filed Oct. 1, 2021 in Japanese Patent Applciation No. 2021-526710, 10 pages.

JPO, Japanese Office Action issued on Aug. 3, 2021 in Japanese Patent Application No. 2021-526710, 5 pages.

To JPO, Amendment filed May 14, 2021 in Japanese Patent Application No. 2021-526710, 8 pages.

WIPO, Japanese International Search Authority, International Search Report (with English translation) and Written Opinion mailed on Mar. 17, 2020 in International Patent Application No. PCT/JP2020/005006, 11 pages.

* cited by examiner

| Psychological state | Parasympathetic dominance | | Sympathetic dominance | | | |
|---|---|---|---|---|---|---|
| | Relaxed state | Bored state | Concentrated state | Excited state | Stressed state | Exhausted state |
| Pulse wave | Less than base line (pulse wave is reduced) | | Equal to or more than base line (pulse wave is increased) | | | |
| Pupil size | Less than base line (pupils become smaller) | | Equal to or more than base line (pupils become larger) | | | |
| Brain wave | Alpha wave | Theta wave | Beta wave | Gamma wave | | |
| Duration | | | | $t<T1$ | $T1 \leqq t<T1+T2$ | $T1+T2 \leqq t$ |

FIG.4

CONTENT PLAYBACK DEVICE, CONTENT PLAYBACK METHOD, AND PROGRAM

RELATED APPLICATIONS

This application is the U.S. National Phase of and claims priority to International Patent Application No. PCT/JP2020/005006, International Filing Date Feb. 7, 2020, entitled *Content Playback Device, Content Playback Method, And Program*, which is incorporated herein by reference in its entirety.

TECHNICAL FIELD

The present invention relates to a content playback device, a content playback method and a program, and more particularly to a content playback device, a content playback method and a program for improving interest in content.

BACKGROUND ART

There is known a stress adaptive control device which includes: a biological information detection part for measuring a physical quantity from a human body; a stress and fatigue degree calculation part for calculating a stress level and a fatigue degree on the basis of the measured values; an output control part for outputting one of drive commands corresponding to the fatigue degree and the stress level; and a drive control part for switching a drive state (speed, software difficulty, etc.) of a game machine or the like corresponding to the drive command (see, for example, Patent Document 1). The entire specification, claims, and drawings of Patent Document 1 shall be incorporated herein by reference.

RELATED ART DOCUMENT

Patent Document

Patent Document 1 is JP 9-22314 A

SUMMARY OF THE INVENTION

Problems to be Solved by the Invention

However, the control device described in Patent Document 1 uniformly reduces stress of a player, even in a case where it is appropriate for the player to feel some stress in a game situation such as when fighting a boss monster. For this reason, there is a problem that the player's interest in the game is reduced.

The present invention has been made to solve the above-mentioned problem. An object of the present invention is to provide a content playback device, a content playback method and a program for improving interest in content.

Means of Solving the Problems

In order to achieve the above object, a content playback device (2) according to a first aspect of the present invention includes: a biological information acquisition part (7) for acquiring biological information of a user; and a control part (81) for setting a psychological state corresponding to a situation of content during playback as a targeted psychological state, specifying a psychological state of the user from the biological information acquired by the biological information acquisition part (7), and changing a mode of the content so that the psychological state specified from the biological information matches the targeted psychological state.

In the content playback device (2) described above, under the condition that the targeted psychological state is a state in which a sympathetic nerve is dominant, when the psychological state specified from the biological information is a state in which a parasympathetic nerve is dominant, the control part (81) may change the mode of the content so as to enhance the sympathetic nerve, and under the condition that the targeted psychological state is a state in which the parasympathetic nerve is dominant, when the psychological state specified from the biological information is a state in which the sympathetic nerve is dominant, the control part (81) may change the mode of the content so as to suppress the sympathetic nerve.

In the content playback device (2) described above, when the psychological state specified from the biological information matches the targeted psychological state, the control part (81) may not change the mode of the content.

In the content playback device (2) described above, the control part (81) may set a base line for determining which one of the sympathetic nerve and the parasympathetic nerve is dominant in the psychological state of the user based on the biological information acquired by the biological information acquisition part (7) before the playback of the content.

In the content playback device (2) described above, when the biological information acquired by the biological information acquisition part (7) during the playback of the content is equal to or greater than the base line, the control part (81) may determine that the sympathetic nerve is dominant, and when the biological information is less than the base line, the control part (81) may determine that the parasympathetic nerve is dominant.

In the content playback device (2) described above, when a brain wave of the user specified from the biological information acquired by the biological information acquisition part (7) is an alpha wave, the control part (81) may specify that the psychological state of the user is a relaxed state, and when the brain wave of the user is a theta wave, the control part (81) may specify that the psychological state of the user is a bored state, and under the condition that the targeted psychological state is the relaxed state, when the psychological state specified from the biological information is the bored state, the control part (81) may change the mode of the content such that the brain wave of the user becomes the alpha wave.

In the content playback device (2) described above, when a brain wave of the user specified from the biological information acquired by the biological information acquisition part (7) is a gamma wave, the control part (81) may specify that the psychological state of the user is an excited state, and when the excited state continues for a predetermined period or longer, the control part (81) may instruct the user to interrupt the playback of the content.

A content playback method according to a second aspect of the present invention comprises:

acquiring biological information of a user by a biological information acquisition part (7), and setting a psychological state corresponding to a situation of content during playback as a targeted psychological state, specifying a psychological state of the user from the biological information acquired by the biological information acquisition part (7), and changing a mode of the content so that the psychological state specified from the biological information matches the targeted psychological state by a control part (81).

A program according to a third aspect of the present invention causes a computer of a content playback device (2) which comprises a biological information acquisition part (7) for acquiring biological information of a user, to execute a process for setting a psychological state corresponding to a situation of content during playback as a targeted psychological state, specifying a psychological state of the user from the biological information acquired by the biological information acquisition part (7), and changing a mode of the content so that the psychological state specified from the biological information matches the targeted psychological state.

Effects of the Invention

According to the present invention, it is possible to provide the content playback device, the content playback method and the program for improving the interest in the content.

BRIEF DESCRIPTION OF THE DRAWINGS

FIG. 4 is an explanatory diagram illustrating a relationship between biological information and a psychological state.

MODE FOR CARRYING OUT THE INVENTION

Hereinafter, the best mode for carrying out the present invention will be described.

First, a configuration of a game system according to the present embodiment of the present invention will be described with reference to the drawings.

Figure 1:
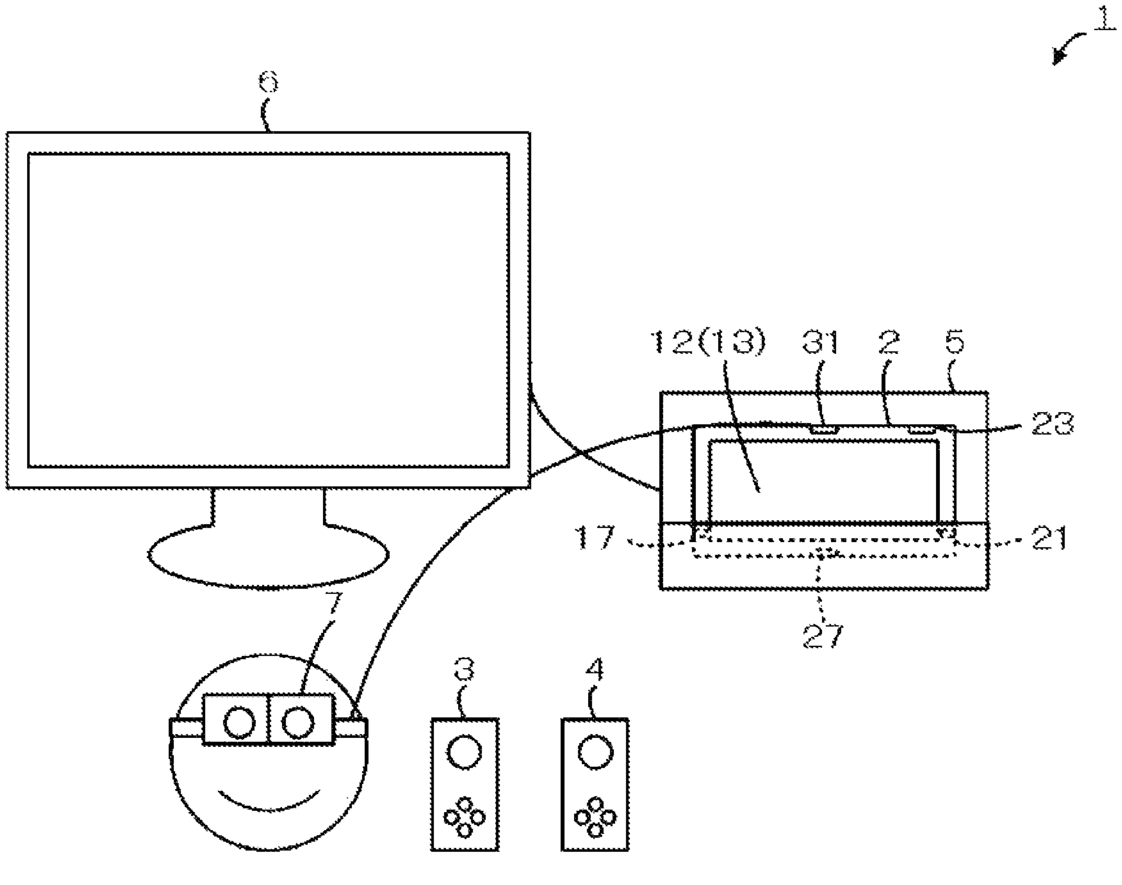
FIG. 1 is a diagram illustrating an overall configuration of a game system according to the present embodiment.

FIG. 1 is a diagram illustrating an overall configuration of a game system according to the present embodiment.

As shown in FIG. 1, a game system 1 is composed of a main body device 2, a left controller 3, a right controller 4, a cradle 5, a stationary monitor 6 and a biological information acquisition device (biological information acquisition part) 7.

In the game system 1, the left controller 3 and the right controller 4 can be attached to and detached from the main body device 2. The left controller 3 and the right controller 4 can be attached to the main body device 2 to be used as an integrated device. However, in the present embodiment, the main body device 2, the left controller 3 and the right controller 4 are used as separate units. When one player uses both the left controller 3 and the right controller 4, the player can use an accessory device that joins the left controller 3 and the right controller 4 to function as one operation device.

The game system 1 can be used as a portable device (for example, a portable game machine), which displays an image on the main body device 2. In the present embodiment, the game system 1 is used as a stationary device (for example, a stationary game machine), which displays an image on the stationary monitor 6 by attaching the main body device 2 to the cradle 5.

The following explanation uses the game system 1 in a use mode in which images (and sound) are outputted from the stationary monitor 6 by attaching the main body device 2 alone to the cradle 5 with the left controller 3 and the right controller 4 detached from the main body device 2.

The biological information acquisition device 7 is a goggle type device for acquiring biological information such as a pulse wave, a brain wave, and a change in pupils of the player, and is mounted on the head of the player.

Figure 2:
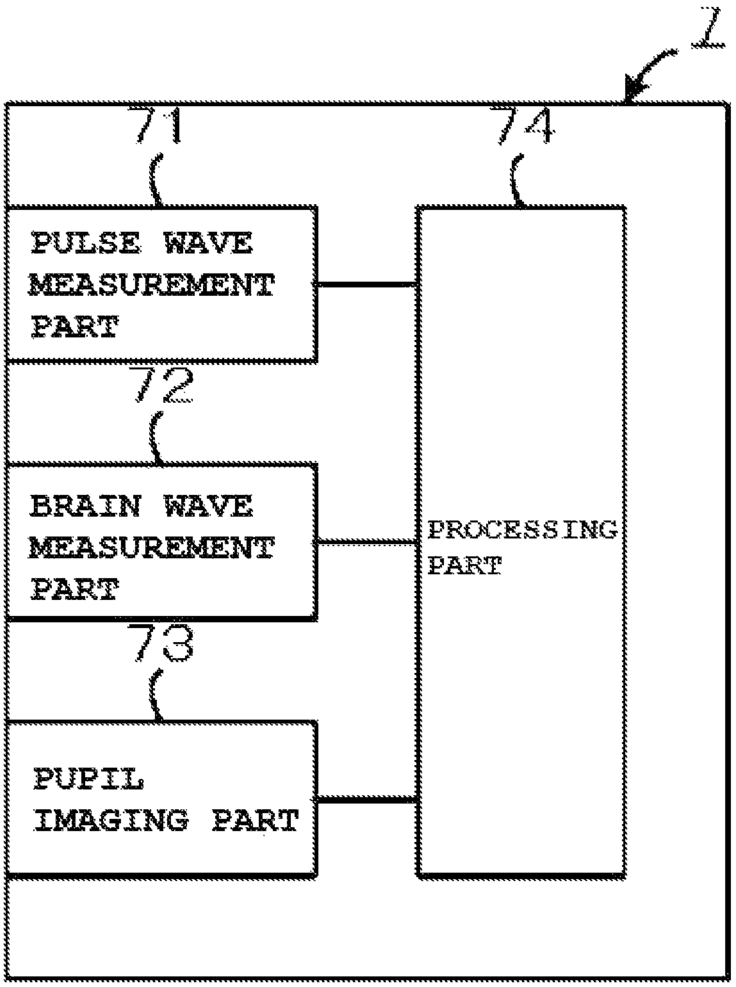
FIG. 2 is a block diagram showing a configuration example of a biological information acquisition device.

FIG. 2 is a block diagram showing a configuration example of a biological information acquisition device.

As shown in FIG. 2, the biological information acquisition device 7 includes a pulse wave measurement part 71, a brain wave measurement part 72, a pupil imaging part 73 and a processing part 74.

The pulse wave measurement part 71 is composed of, for example, an infrared LED (Light Emitting Diode) that emits infrared light having a predetermined wavelength (for example, 940 nm), and an infrared photo register that receives reflected light of the emitted infrared light. The pulse wave measurement part 71 is provided in the vicinity of the temple of the player, and measures the pulse (pulse wave) of the player based on light absorption by hemoglobin in the blood vessel under the skin. Specifically, the pulse wave measurement part 71 emits the infrared light to the skin near the temple of the player from the infrared LED, and receives the reflected light with the infrared photo register. Then, the pulse wave measurement part 71 detects the pulse (pulse wave) of the player by converting a light amount of the infrared light into a photoelectric signal. For example, when the blood flow rate in the vicinity of the temple of the player increases, the detected value of the pulse wave measurement part 71 increases. Further, when the blood flow rate decreases, the detected value of the pulse wave measurement part 71 decreases. As described above, a pulse wave portion in which the detected values of the pulse wave measurement part 71 pulsate is generated as a pulse wave signal and is outputted to the processing part 74.

The brain wave measurement part 72 is composed of, for example, a plurality of electrodes. The brain wave measurement part 72 is attached to the head of the player to be measured of the brain wave. The brain wave measurement part 72 detects the brain wave of the player by making contact with each of the predetermined number of points at the head of the player (e.g., the forehead, behind the left ear, behind the right ear, back of the head, etc.), and outputs the detected value (brain wave signal) to the processing part 74.

The pupil imaging part 73 is composed of, for example, an infrared camera. The pupil imaging part 73 is disposed in the vicinity of the rim of the goggle. Further, the pupil imaging part 73 photographs the pupils of the player looking at an image displayed on the stationary monitor 6, and outputs a pupil image obtained by the photographing to the processing part 74.

The processing part 74 is composed of, for example, an MCU (Micro Controller Unit). The processing part 74 controls the amount of infrared light emitted from the infrared LED of the pulse wave measurement part 71 and generates pulse wave data by A/D converting the pulse wave signal outputted from the pulse wave measurement part 71. The processing part 74 analyzes the brain wave signal outputted from the brain wave measurement part 72. Further, the processing part 74 extracts a predetermined frequency band used in the game (for example, a frequency band of a wave to be used such as an alpha wave, a beta wave, a gamma wave or a theta wave) to generate brain wave data. Furthermore, the processing part 74 analyzes the size of the pupil diameter of the player in the pupil image obtained by the pupil imaging part 73 and the change thereof to generate pupil data. Then, the processing part 74 sequentially outputs biological data including the pulse wave data, the brain wave data and the pupil data to the main body device 2 via a connection cable (not shown).

The main body device 2 shown in FIG. 1 is a device that executes various processes (e.g., the game processing) in the game system 1. The main body device 2 includes: a display 12; a touch panel 13 on a screen of the display 12; a left terminal 17 for wired communication with the left controller 3; a right terminal 21 for wired communication with the right controller 4; a slot 23; a lower terminal 27; an upper terminal 31 for communicating with the biological information acquisition device 7; and a speaker (not shown).

The display 12 displays an image generated by the main body device 2. In the present embodiment, the display 12 is a liquid crystal display (LCD) device. However, the display 12 may be any type of display device. In the present embodiment, the touch panel 13 is configured to allow a method in which a multi-touch input is possible (for example, a capacitance method). However, the touch panel 13 may be any type, for example, allowing a method in which a single touch input is possible (for example, a resistive film method).

The slot 23 has a configuration in which a predetermined type of storage medium can be mounted. The predetermined type of storage medium is, for example, a storage medium (e.g., a dedicated memory card) dedicated to the game system 1 and the same type of information processing device. For example, the predetermined type of storage medium is used for storing data used in the main body device 2 (e.g., saved data of an application) and/or a program executed by the main body device 2 (e.g., a program of an application).

The lower terminal 27 is a terminal for the main body device 2 to communicate with the cradle 5. In the present embodiment, the lower terminal 27 is a USB connector (more specifically, a female connector). When the main body device 2 is placed on the cradle 5, the game system 1 can display an image generated and outputted by the main body device 2 on the stationary monitor 6.

Figure 3:
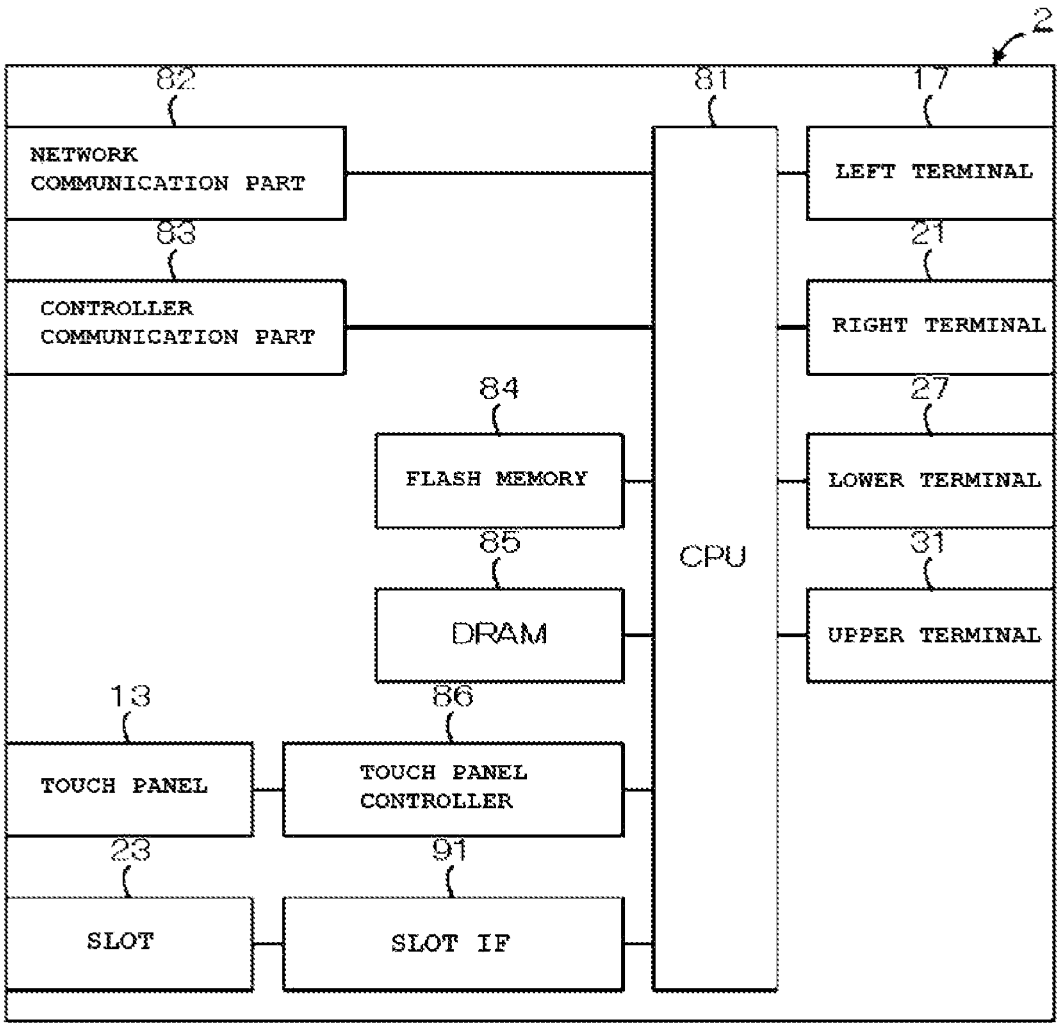
FIG. 3 is a block diagram showing an example of an internal configuration of a main body device.

FIG. 3 is a block diagram showing an example of an internal configuration of a main body device.

As shown in FIG. 3, the main body device 2 includes a CPU (Central Processing Unit) (control part) 81, a network communication part 82, a controller communication part 83, a flash memory 84, a DRAM (Dynamic Random Access Memory) 85, a touch panel controller 86 and a slot interface (hereinafter referred to as "I/F") 91.

The CPU 81 is an information processing part that executes various types of information processes executed in the main body device 2. The CPU 81 executes various types of information processes by executing an information process program (for example, a game program) stored in a storage part (specifically, an internal storage medium such as the flash memory 84 or an external storage medium attached to the slot 23), and appropriately reading or writing data between the flash memory 84, the DRAM 85 and the storage medium.

The CPU 81 is connected to the display 12. On the display 12, an image generated (for example, by executing various types of information processes) and/or an image acquired from the outside are displayed by the CPU 81.

Further, the CPU 81 is connected to the left terminal 17, the right terminal 21, the lower terminal 27 and the upper terminal 31. When the CPU 81 performs wired communication with the left controller 3, the CPU 81 transmits data to the left controller 3 via the left terminal 17, and receives operation data from the left controller 3 via the left terminal 17. When the CPU 81 performs wired communication with the right controller 4, the CPU 81 transmits data to the right controller 4 via the right terminal 21, and receives operation data from the right controller 4 via the right terminal 21. When the CPU 81 communicates with the cradle 5, the CPU 81 transmits data to the cradle 5 via the lower terminal 27. As described above, when the main body device 2 is attached to the cradle 5, the main body device 2 can output data (for example, image data and audio data) to the stationary monitor 6 via the cradle 5. When the CPU 81 communicates with the biological information acquisition device 7, the CPU 81 receives the biological data from the biological information acquisition device 7 via the upper terminal 31.

The network communication part 82 is connected to the CPU 81. The network communication part 82 communicates (specifically, wirelessly communicates) with an external device via a network. In the present embodiment, the network communication part 82 communicates with the external device through the wireless LAN using a method conforming to the Wi-Fi standard as a first communication mode. In addition, the network communication part 82 wirelessly communicates with other main body devices 2 of the same type using a predetermined communication method (for example, communication by a unique protocol or infrared communication) as a second communication mode. In the wireless communication according to the second communication mode, the wireless communication can be performed with other main body devices 2 disposed in a closed local network area to realize a function of enabling so-called "local communication" in which data is transmitted and received by direct communication between the plurality of main body devices 2.

The controller communication part 83 is connected to the CPU 81. The controller communication part 83 performs wireless communication with the left controller 3 and/or the right controller 4. A communication method between the main body device 2, the left controller 3 and the right controller 4 is arbitrary. In the present embodiment, the controller communication part 83 communicates with the left controller 3 and with the right controller 4 in accordance with the Bluetooth (registered trademark) standard. As described above, in the present embodiment, the main body device 2 can perform both wired communication and wireless communication with the left controller 3 and the right controller 4, respectively.

The flash memory 84 and the DRAM 85 are connected to the CPU 81. The flash memory 84 is a memory mainly used to store various types of data (which may be programs) stored in the main body device 2. The DRAM 85 is a memory used to temporarily store various types of data used in the information processes.

In the present embodiment, the DRAM 85 stores a psychological state flag indicating a psychological state to be targeted. The psychological state flag is set to “0” indicating a “relaxed state” in the initial state. When the targeted psychological state is a “concentrated state”, the psychological state flag is set to “1” indicating the “concentrated state”. When the targeted psychological state is an “excited state”, the psychological state flag is set to “2” indicating the “excited state”. When the targeted psychological state is a “stressed state”, the psychological state flag is set to “3” indicating the “stressed state”.

The touch panel controller 86 is a circuit for controlling the touch panel 13. The touch panel controller 86 is connected between the touch panel 13 and the CPU 81. On the basis of a signal from the touch panel 13, the touch panel controller 86 generates data indicating, for example, a position at which a touch input is performed, and outputs the data to the CPU 81.

The slot I/F 91 is connected to the CPU 81. The slot I/F 91 is connected to the slot 23, and reads and writes data for a predetermined type of storage medium (for example, a dedicated memory card) attached to the slot 23 in accordance with an instruction from the CPU 81.

In the present embodiment, the CPU 81 executes game processing by executing a game program stored in the external storage medium or the like attached to the slot 23. In this game processing, a story or scenario to be a core is set in advance, and an action roll playing game in which the game is advanced along the story or scenario is executed.

In the game processing, the CPU 81 sequentially receives the biological data from the biological information acquisition device 7 via the upper terminal 31. Before the game is started, the CPU 81 acquires (calibrates) initial values of pulse wave and pupil size of the player (initial values of the biological information), while outputting healing music or displaying a beautiful photograph or the like so as to bring the psychological state of the player into the “relaxed state”. Then, the CPU 81 sets the base line for determining whether the sympathetic nerve is dominant or the parasympathetic nerve is dominant based on the initial values of pulse wave and pupil size of the player.

After the game is started, the CPU 81 sets the targeted psychological state to the psychological state flag in accordance with a situation of the game being played (the content during playback). Specifically, when the situation is that a character is moving and searching in grassland, the CPU 81 sets “1” indicating the “concentrated state” to the psychological state flag as the targeted psychological state. When the situation is that the character is fighting a monster or moving and exploring dungeons, the CPU 81 sets “2” indicating the “excited state” to the psychological state flag as the targeted psychological state. Further, when the situation is that the character is fighting a boss monster in the dungeons, the CPU 81 sets “3” indicating the “stressed state” to the psychological state flag as the targeted psychological state. Then, when the situation is that a scene is changed to proceed with a new map after the game is cleared, the CPU 81 sets “0” indicating the “relaxed state” to the psychological state flag as the targeted psychological state.

Further, the CPU 81 specifies the psychological state of the player from the combination of the biological information such as the pulse wave, the brain wave and the change in the pupils of the player. Specifically, the CPU 81 determines whether or not the pulse wave of the player specified from the pulse wave data included in the biological data is equal to or greater than the base line. Further, the CPU 81 determines whether the brain wave of the player specified from the brain wave data included in the biological data is any of the alpha wave, the beta wave, the gamma wave and the theta wave. Furthermore, the CPU 81 determines whether or not the pupil size of the player specified from the pupil data included in the biological data becomes larger than or equal to the base line. Then, the CPU 81 specifies the psychological state of the player from the combination of the biological information such as the pulse wave, the brain wave and the change in the pupils of the player determined as described above.

FIG. 4 is an explanatory diagram illustrating a relationship between biological information and a psychological state.

As shown in FIG. 4, in a case where both the pulse wave and the pupil size of the player are less than the base line (when the pulse wave is reduced and the pupils become smaller), that is, in a case where the parasympathetic nerve is dominant, the CPU 81 determines that the psychological state of the player is the “relaxed state”, if the brain wave of the player is the alpha wave. On the other hand, in the above case, the CPU 81 determines that the psychological state of the player is the “bored state”, if the brain wave of the player is the theta wave. In contrast, in a case where both the pulse wave and the pupil size of the player are equal to or more than the base line (when the pulse wave is increased and the pupils become larger), that is, in a case where the sympathetic nerve is dominant, the CPU 81 determines that the psychological state of the player is the “excited state”, if the brain wave of the player is the beta wave. On the other hand, in the above case, the CPU 81 determines that the psychological state of the player is the “concentrated state”, if the brain wave of the player is the gamma wave. Further, if duration t of the “excited state” is equal to or greater than T1, the CPU 81 determines that the psychological state of the player is the “stressed state”, and if the “stressed state” continues for more than T2, that is, if the “excited state” continues for the predetermined period T1+T2 or more, the CPU 81 determines that the psychological state of the player is the “exhausted state”.

Then, the CPU 81 changes the game mode so that the psychological state is made to the targeted psychological state.

Specifically, under the condition that “1” indicating the “concentrated state” is set to the psychological state flag, when the psychological state of the player is the “relaxed state” or the “bored state”, the game mode is changed so that the sympathetic nerve is enhanced and the sympathetic nerve becomes dominant in order to bring the psychological state of the player to the “concentrated state”, assuming that the player shows a sign of boredom. For example, a group of animals different from the monsters may appear, or a relatively weak monster may appear.

In contrast, when the psychological state of the player matches the psychological state set to the psychological state flag, that is, the “concentrated state”, the game mode is not changed so as to maintain the “concentrated state”. In other words, as usual, a wide space and grassland scenery are displayed, and mild BGM and natural environmental sounds are outputted.

On the other hand, when the psychological state of the player is the “stressed state”, the game mode is changed so that the sympathetic nerve is suppressed in order to return the psychological state of the player to the “concentrated state”. For example, a special scene for cool down is displayed in the game.

In addition, when the psychological state of the player is “exhausted state”, the screen for giving advice (instruction) so as to interrupt the game and rest his/her body is displayed, assuming that it is impossible to immediately return the psychological state of the player to the “concentrated state”.

Under the condition that “2” indicating the “excited state” is set to the psychological state flag, when the psychological state of the player is any of the “relaxed state”, the “bored state” and the “concentrated state”, the game mode is changed so that the sympathetic nerve is enhanced in order to bring the psychological state of the player to the “excited state”. For example, if the battle with a monster is being performed, a reinforcement monster will appear. Further, if the moving and exploring in dungeons are being performed, sound effects will be outputted or monsters will suddenly appear.

In contrast, when the psychological state of the player matches the psychological state set to the psychological state flag, that is, the “excited state”, the game mode is not changed so as to maintain the “excited state”. In other words, as usual, the background music or sound effects with a disturbing atmosphere to cause anxiety or tension will be left playing, if the moving and exploring in dungeons are being performed.

On the other hand, when the psychological state of the player is the “stressed state”, the game mode is changed so that the sympathetic nerve is suppressed in order to return the psychological state of the player to the “excited state”, assuming that a load to the player is too large. For example, if the battle is being performed, the strength of the monsters is lowered. Further, if the moving and exploring in dungeons are being performed, a clue indicating a correct route is displayed.

In addition, when the psychological state of the player is the “exhausted state”, the screen for giving advice so as to interrupt the game and rest his/her body is displayed, assuming that it is impossible to immediately return the psychological state of the player to the “excited state”.

Under the condition that “3” indicating the “stressed state” is set to the psychological state flag, when the psychological state of the player is any of the “relaxed state”, the “bored state”, the “concentrated state” and the “excited state”, the game mode is changed so that the sympathetic nerve is enhanced in order to bring the psychological state of the player to the “stressed state”. For example, a reinforcement monster is allowed to appear, a boss monster is temporarily reinforced, or conversely, the character is temporarily weakened.

On the other hand, when the psychological state of the player is the “stressed state”, the game mode is not changed in order to maintain the “stressed state”. In this regard, for maintaining the “stressed state”, the game mode may be changed in such a way that the psychological state of the player is prevented from becoming “exhausted state” by performing certain support, for example, releasing a disadvantageous condition (e.g., paralysis of the character) or giving the character an advantageous item, while the psychological state of the player is prevented from returning to the “relaxed state”, the “bored state”, the “concentrated state” and the “excited state” by not performing excessive support.

In addition, when the psychological state of the player is the “exhausted state”, the screen for giving advice so as to interrupt the game and rest his/her body is displayed, assuming that it is impossible to immediately return the psychological state of the player to the “stressed state”.

Under the condition that “0” indicating the “relaxed state” is set to the psychological state flag, when the psychological state of the player matches the psychological state set to the psychological state flag, that is, the “relaxed state”, the game mode is not changed in order to maintain the “relaxed state”, assuming that the player is calm. For example, as usual, a wide space and grassland scenery are displayed, and mild BGM and natural environmental sounds are outputted. Then, after a predetermined period of time, a battle with monsters or a new quest will be generated.

In contrast, when the psychological state of the player is the “bored state”, the game mode is changed so that the brain wave becomes the alpha wave in order to bring the psychological state of the player to the “relaxed state”. For example, a group of animals different from the monsters may appear, or a natural environmental sound or a change in scenery may be generated.

On the other hand, when the psychological state of the player is any of the “concentrated state”, the “excited state” and the “stressed state”, the game mode is changed so that the sympathetic nerve is suppressed and the parasympathetic nerve becomes dominant in order to return the psychological state of the player to the “relaxed state”. For example, a wide space and grassland scenery are displayed, and mild BGM and natural environmental sounds are outputted.

In addition, when the psychological state of the player is the “exhausted state”, the screen for giving advice so as to interrupt the game and rest his/her body is displayed, assuming that it is impossible to immediately return the psychological state of the player to the “relaxed state”.

Next, the game processing executed by the game system 1 having the above-described configuration will be described with reference to the drawings.

The CPU 81 executes the game processing by executing a game program stored in the external storage medium or the like attached to the slot 23.

Figure 5:
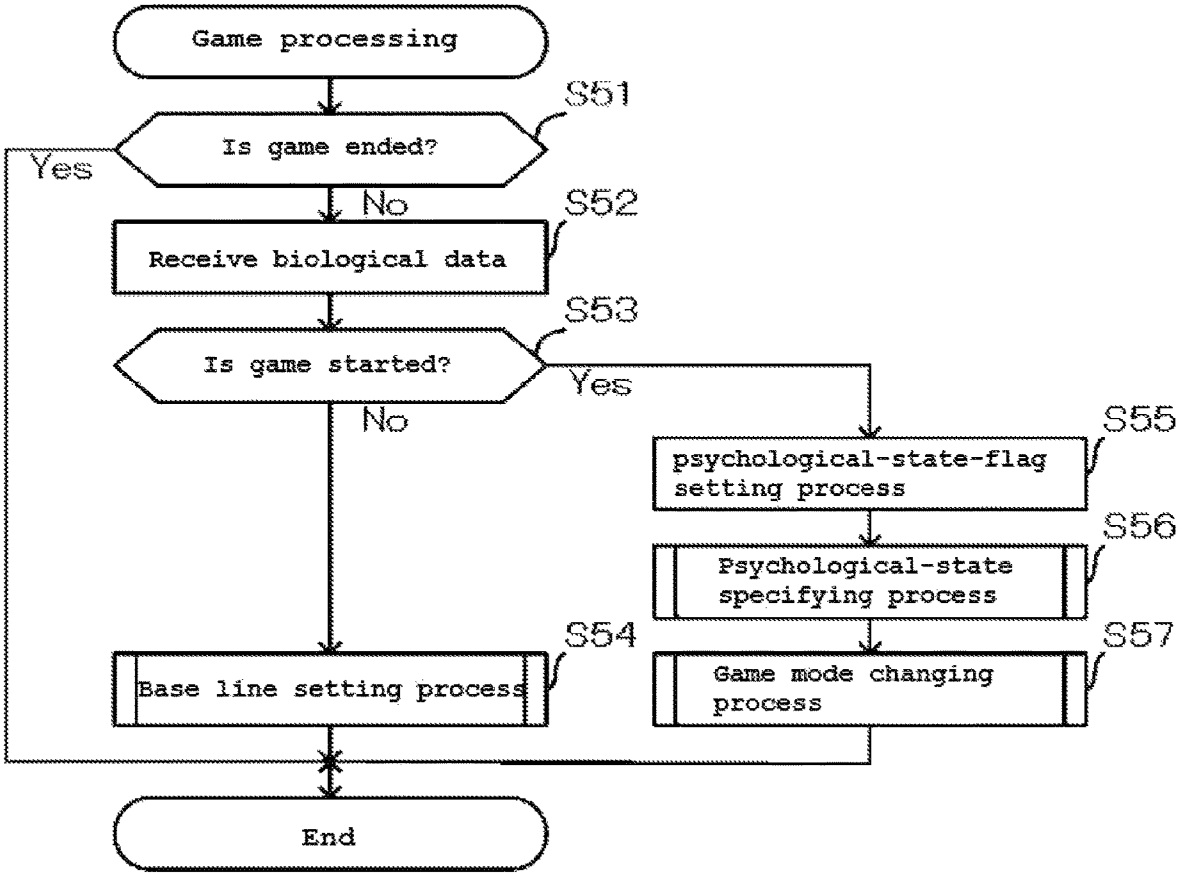
FIG. 5 is a flowchart showing details of game processing.

FIG. 5 is a flowchart showing details of game processing. In the game processing shown in FIG. 5, the CPU 81 determines whether or not the game ends (step S51).

If the game ends (YES in step S51), the CPU 81 makes the game processing finish.

If the game does not end (NO in step S51), the CPU 81 sequentially receives the biological data from the biological information acquisition device 7 via the upper terminal 31 (step S52).

In addition, the CPU 81 determines whether or not the game is started (step S53).

If it is before the start of the game (NO in step S53), the CPU 81 executes a base line setting process for setting the base line for determining whether the sympathetic nerve is dominant or the parasympathetic nerve is dominant (step S54).

Figure 6:
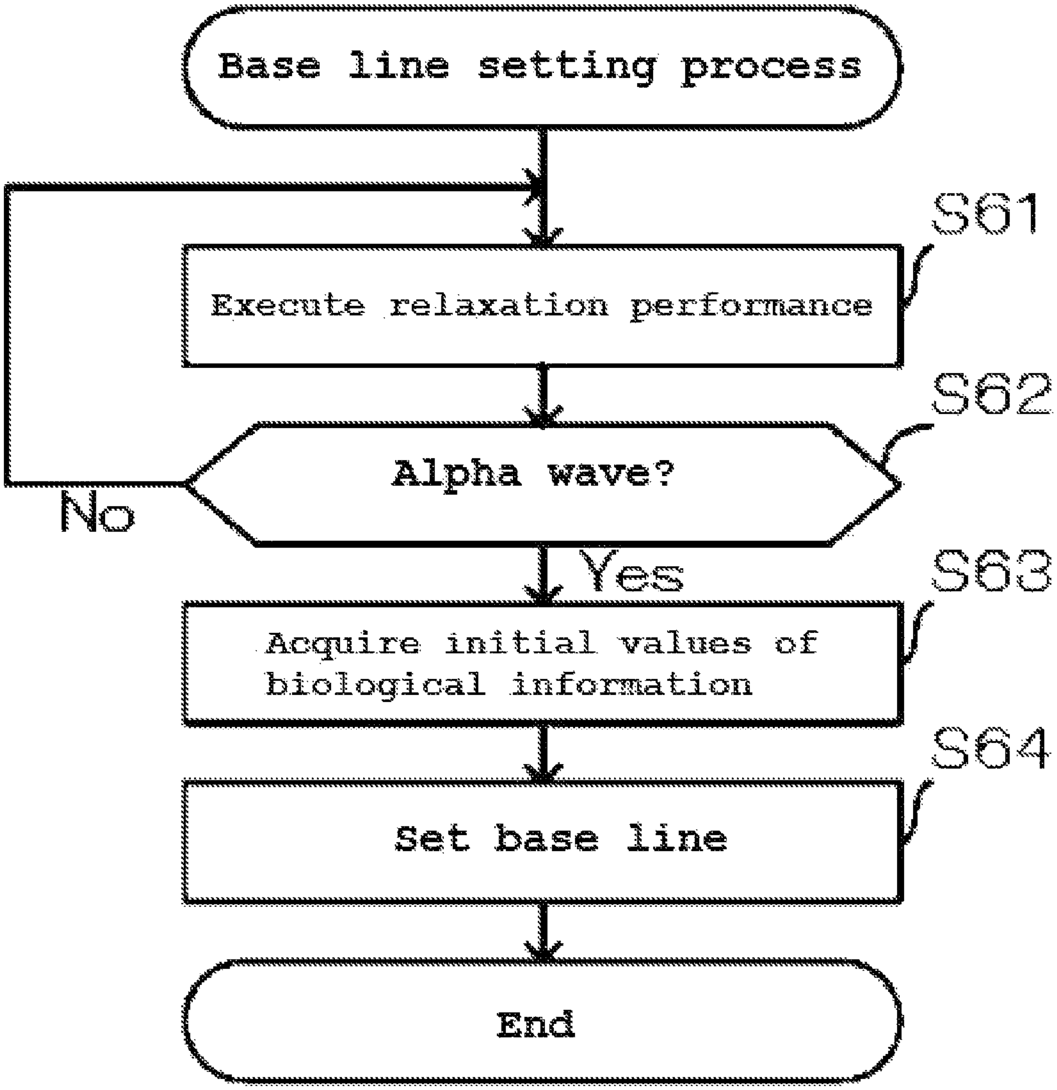
FIG. 6 is a flowchart showing details of a base line setting process.

FIG. 6 is a flowchart showing details of a base line setting process.

When the base line setting process shown in FIG. 6 is started, the CPU 81 first executes a performance (relaxation performance) for bringing the psychological state of the player to the “relaxed state” (step S61).

Next, the CPU 81 determines whether or not the brain wave of the player specified from the brain wave data included in the biological data is the alpha wave (step S62).

If the brain wave of the player is other than the alpha wave (step S62; NO), the CPU 81 returns to step S61. On the other hand, if the brain wave of the player is the alpha wave (step S62; YES), the CPU 81 acquires, as the initial values of the biological information, the pulse wave and the pupil size of the player being in the “relaxed state” from the pulse wave data and the pupil data included in the biological data, assuming that the psychological state of the player is the “relaxed state” (step S63).

Then, the CPU 81 sets the base line based on the initial values of the pulse wave and the pupil size of the player acquired in step S63 (step S64), and then ends the base line setting process.

On the other hand, if the game is started (step S53 shown in FIG. 5; Yes), the CPU 81 executes a psychological-state-flag setting process for setting the targeted psychological state to the psychological state flag in accordance with the game situation (step S55).

Subsequently, the CPU 81 executes a psychological-state specifying process for specifying the psychological state of the player from the combination of the biological information such as the pulse wave, the brain wave and the change in the pupils of the player (step S56).

Figure 7:
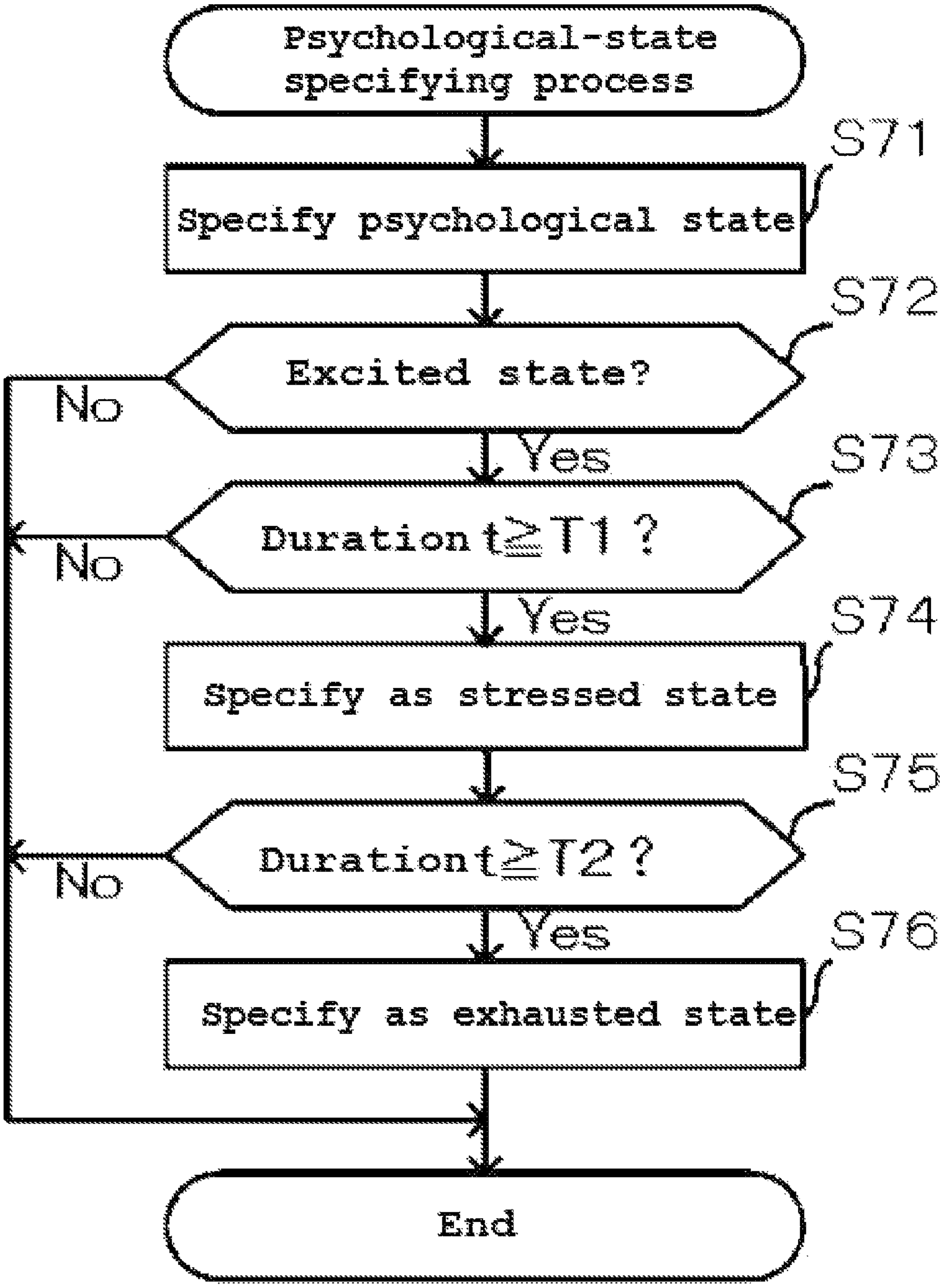
FIG. 7 is a flowchart showing details of a psychological-state specifying process.

FIG. 7 is a flowchart showing details of a psychological-state specifying process.

When the psychological-state specifying process shown in FIG. 7 is started, the CPU 81 specifies the psychological state of the player as one of the "relaxed state", the "bored state", the "concentrated state" and the "excited state" based on the combination of the biological information such as the pulse wave, the brain wave and the change in the pupils of the player included in the biological data (step S71).

If the psychological state of the player specified in step S71 is other than the "excited state" (step S72; NO), the CPU 81 makes the psychological-state specifying process finish as it is.

On the other hand, if the psychological state of the player is the "excited state" (step S72; YES), the CPU 81 determines whether or not the duration t of the "excited state" is equal to or greater than T1 (step S73).

If the duration t of the "excited state" is less than T1 (step S73; NO), the CPU 81 makes the psychological-state specifying process finish as it is.

On the other hand, if the duration t of the "excited state" is equal to or greater than T1 (step S73; YES), the CPU 81 specifies that the psychological state of the player is the "stressed state" (step S74).

Then, the CPU 81 determines whether or not the "stressed state" continues for T2 or more, that is, whether or not the duration t of the "excited state" continues for the predetermined period T1+T2 or more (step S75).

If the duration t of the "excited state" is less than the predetermined period T1+T2 (step S75; NO), the CPU 81 makes the psychological-state specifying process finish as it is.

On the other hand, if the duration t of the "excited state" is equal to or greater than the predetermined period T1+T2 (step S75; YES), the CPU 81 specifies that the psychological state of the player is the "exhausted state" (step S76), and makes the psychological-state specifying process finish.

Then, the CPU 81 executes a game mode changing process for changing the game mode in order to achieve the targeted psychological state set to the psychological state flag (step S57 shown in FIG. 5).

Figure 8:
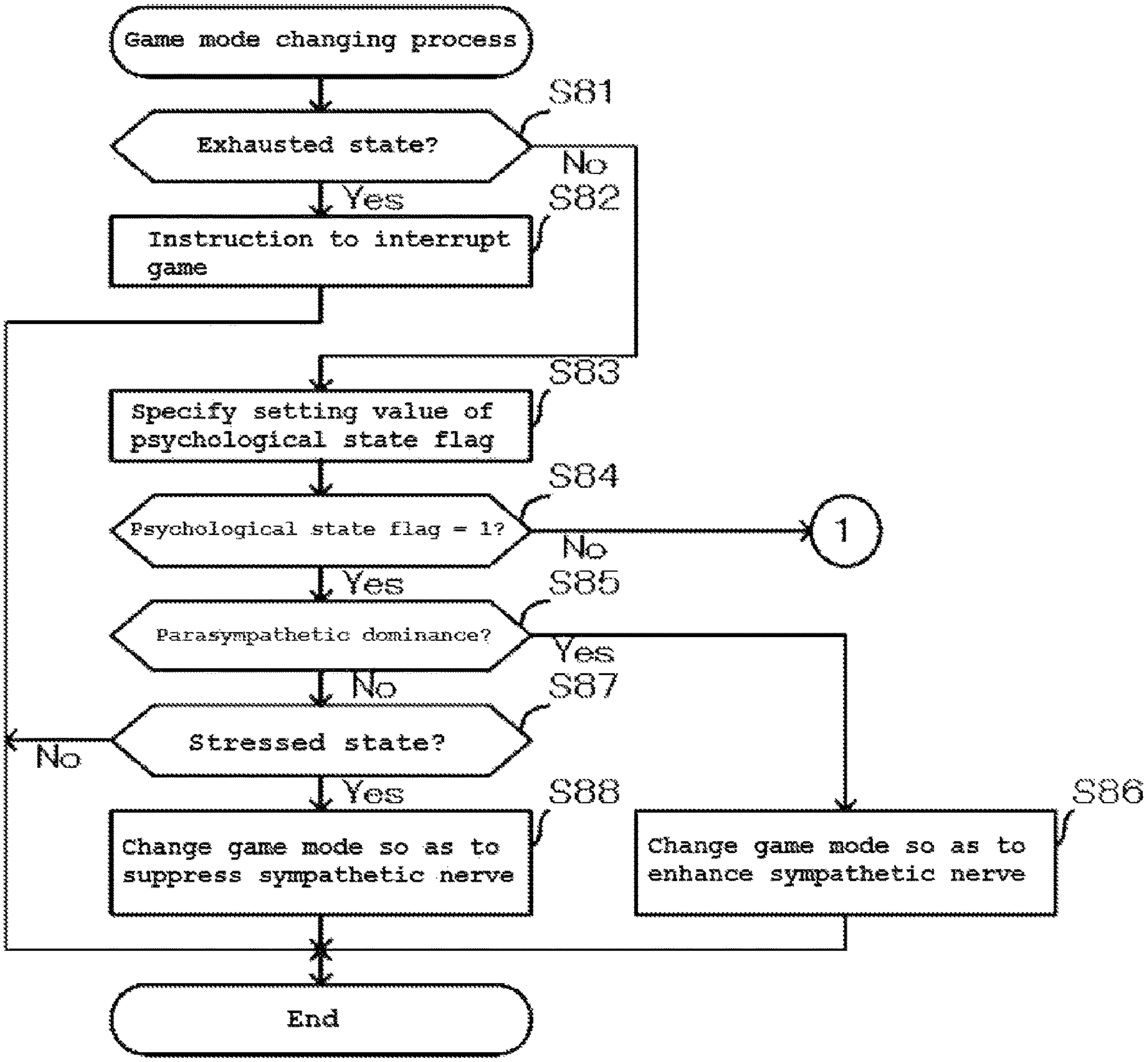
FIG. 8 is a flowchart showing details of a game mode changing process.
Figure 9:
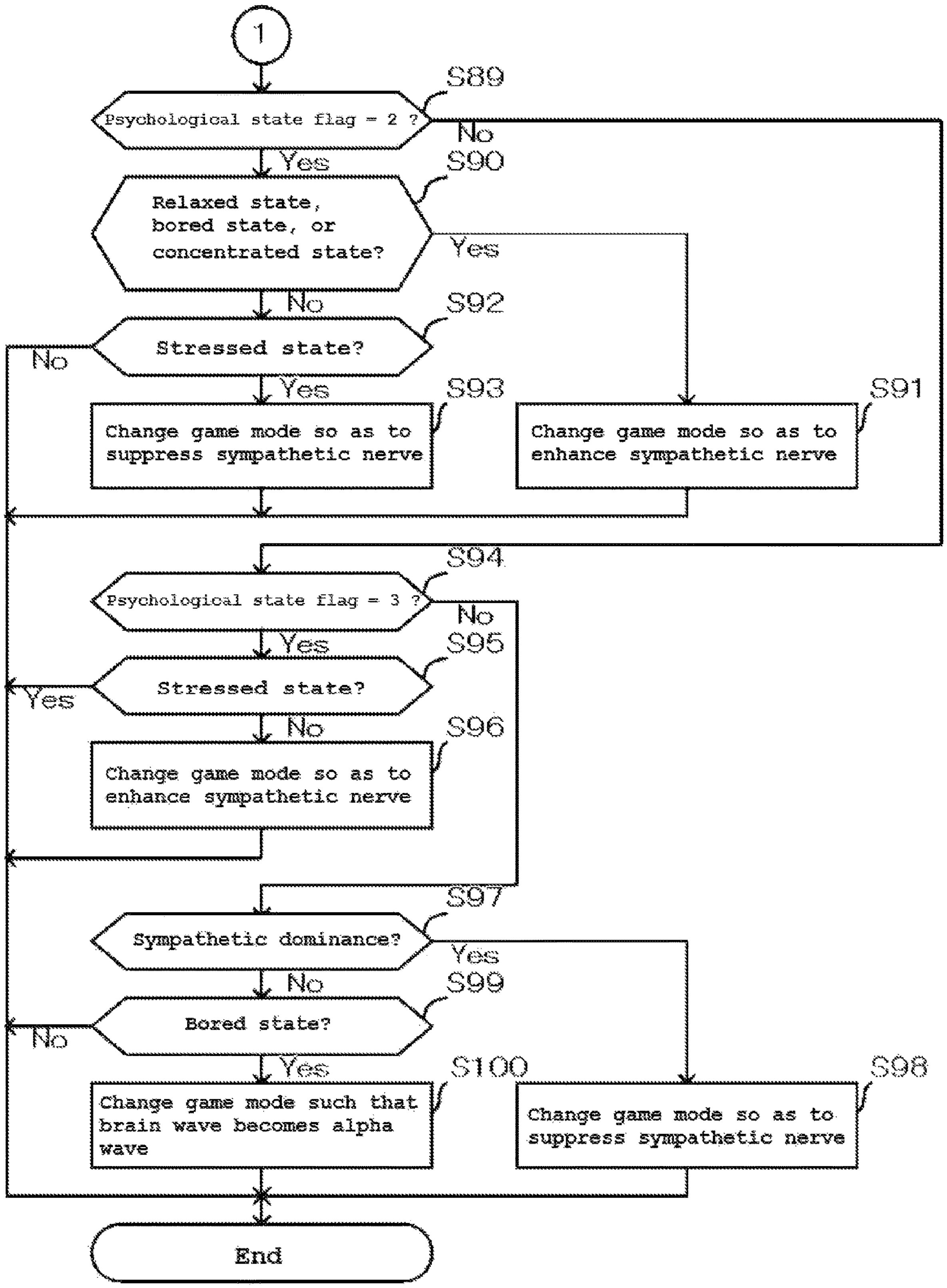
FIG. 9 is a flowchart showing a continuation of the game mode changing process.

FIG. 8 and FIG. 9 are flowcharts showing details of a game mode changing process.

In the game mode changing process shown in FIG. 8 and FIG. 9, the CPU 81 first determines whether the psychological state of the player specified by the psychological-state specifying process in step S56 is the "exhausted state" (step S81 shown in FIG. 8).

When the psychological state of the player is the "exhausted state" (step S81; YES), the screen for giving advice (instruction) so as to interrupt the game is displayed (step S82), assuming that it is impossible to immediately return the psychological state of the player to the psychological states other than the "exhausted state", and then the game mode changing process is finished.

If the psychological state of the player is other than the "exhausted state" (step S81; NO), the CPU 81 specifies the setting value of the psychological state flag (step S83).

Under the condition that "1" indicating the "concentrated state" is set to the psychological state flag (step S84; YES), when the parasympathetic nerve is a dominant state such that the psychological state of the player is either the "relaxed state" or the "bored state" (step S85; Yes), the CPU 81 enhances the sympathetic nerve in order to bring the psychological state of the player to the "concentrated state" (step S86), and then makes the game mode changing process finish (step S86).

On the other hand, if the psychological state of the player is the "stressed state" (step S85; NO, step S87; YES), the CPU 81 changes the game mode such that the sympathetic nerve is suppressed in order to return the psychological state of the player to the "concentrated state" (step S88), and then makes the game mode changing process finish.

On the other hand, if the psychological state of the player matches the psychological state set to the psychological state flag, that is, the "concentrated state" (step S87; NO), the CPU 81 makes the game mode changing process finish without changing the game mode in order to maintain the "concentrated state".

Under the condition that "2" indicating the "excited state" is set to the psychological state flag (step S84; No, step S89 shown in FIG. 9; Yes), when the psychological state of the player is any of the "relaxed state", the "bored state" and the "concentrated state" (step S90; YES), the CPU 81 changes the game mode such that the sympathetic nerve is enhanced in order to bring the psychological state of the player to the "excited state" (step S91), and then makes the game mode changing process finish.

On the other hand, if the psychological state of the player is the "stressed state" (step S90; NO, step S92; YES), the CPU 81 changes the game mode such that the sympathetic nerve is suppressed in order to return the psychological state of the player to the "excited state" (step S93), and then makes the game mode changing process finish.

In contrast, if the psychological state of the player matches the psychological state set to the psychological state flag, that is, the "excited state" (step S92; NO), the CPU 81 makes the game mode changing process finish without changing the game mode in order to maintain the "excited state".

Under the condition that "3" indicating the "stressed state" is set to the psychological state flag (step S89; No, step S94; YES), when the psychological state of the player is one of the "relaxed state", the "bored state", the "concentrated state" and the "excited state", that is, other than the "stressed state" (step S95; NO), the CPU 81 changes the game mode such that the sympathetic nerve is enhanced in order to bring the psychological state of the player to the "stressed state" (step S96), and then makes the game mode changing process finish.

On the other hand, if the psychological state of the player is the "stressed state" (step S95; YES), the CPU 81 makes the game mode changing process finish without changing the game mode in order to maintain the "stressed state".

Under the condition that "0" indicating the "relaxed state" is set to the psychological state flag (step S94; No), when the sympathetic nerve is in a dominant state such that the psychological state of the player is the "concentrated state", the "excited state" or the "stressed state" (step S97; YES), the CPU 81 changes the game mode such that the sympathetic nerve is suppressed and the parasympathetic nerve becomes a dominant state in order to return the psychological state of the player to the "relaxed state" (step S98), and then makes the game mode changing process finish.

On the other hand, if the psychological state of the player is the "bored state" (step S97; NO, step S99; YES), the CPU 81 changes the game mode such that the brain wave becomes the alpha wave in order to bring the psychological state of the player to the "relaxed state" (step S100), and then makes the game mode changing process finish.

In contrast, if the psychological state of the player matches the psychological state set to the psychological state flag, that is, the "relaxed state" (step S99; NO), the CPU 81 makes the game mode changing process finish without changing the game mode in order to maintain the "relaxed state".

As described above, the main body device 2 according to the present embodiment includes: the biological information acquisition device 7 for acquiring the biological information of the player who is the user of the game system 1; and the CPU 81 which is the control part. The CPU 81 sets the psychological state corresponding to the situation of the game being played to the psychological state flag as the psychological state to be targeted. Subsequently, the CPU 81 specifies the psychological state of the player from the biological information acquired by the biological information acquisition device 7. Then, the CPU 81 changes the game mode so that the psychological state specified from the biological information matches the psychological state set as the target. Thus, the main body device 2 can improve the interest for the game by bringing the psychological state of the player to the psychological state corresponding to the situation of the game being played.

Specifically, under the condition that the psychological state set as the target is a state in which the sympathetic nerve is dominant such as the "concentrated state" or the "excited state", when the psychological state specified from the biological information is a state in which the parasympathetic nerve is dominant such as the "relaxed state" or the "bored state", the CPU 81 changes the game mode such that the sympathetic nerve is enhanced. On the other hand, under the condition that the psychological state set as the target is a state in which the parasympathetic nerve is dominant, such as the "relaxed state" or the "bored state", when the sympathetic nerve is dominant such that the psychological state specified from the biological information is the "concentrated state" or the "excited state", the CPU 81 changes the game mode such that the sympathetic nerve is suppressed. In contrast, when the psychological state specified from the biological information matches the psychological state set as the target, the CPU 81 does not change the game mode. In this way, the main body device 2 can improve the interest for the game by bringing the psychological state of the player to the psychological state corresponding to the situation of the game being played.

Further, the CPU 81 sets the base line for determining which one of the sympathetic nerve and the parasympathetic nerve is dominant in the psychological state of the player based on the biological information acquired by the biological information acquisition device 7 before the start of the game. When the biological information acquired by the biological information acquisition device 7 during the play of the game is equal to or greater than the base line, the CPU 81 determines that the sympathetic nerve is dominant. Further, when the biological information is less than the base line, the CPU 81 determines that the parasympathetic nerve is dominant. As described above, based on the biological information acquired before the start of the game, the main body device 2 can accurately set the base line for determining which one of the sympathetic nerve and the parasympathetic nerve is dominant in the psychological state of the player.

When the brain wave of the player specified from the biological information acquired by the biological information acquisition device 7 is the alpha wave, the CPU 81 specifies that the psychological state of the player is the relaxed state. Further, when the brain wave of the player is the theta wave, the CPU 81 specifies that the psychological state of the player is the bored state. Under the condition that the psychological state set as the target is the relaxed state, when the psychological state specified from the biological information is the bored state, the CPU 81 changes the game mode such that the brain wave of the player becomes the alpha wave. Thus, the main body device 2 can prevent the player from getting bored in the game.

When the brain wave of the player specified from the biological information acquired by the biological information acquisition device 7 is the gamma wave, the CPU 81 specifies that the psychological state of the player is the excited state. When the excited state continues for the predetermined period T1+T2 or more, the CPU 81 instructs the player to interrupt the play of the game, assuming that the psychological state of the player (user) is in the exhausted state and it is difficult to bring the psychological state of the player to the psychological state set as the target. As described above, the main body device 2 allows the player to interrupt the game to restore the player's fatigue early. After the game is restarted, the main body device 2 can bring the psychological state of the player to the psychological state set as the target.

The present invention is not limited to the above-described embodiment, and various modifications and applications can be made. Hereinafter, the modifications of the above-described embodiment applicable to the present invention will be described.

In the above-described embodiment, the content is described as the game. However, the present invention is not limited thereto, and the content is arbitrary as long as it is a set of information that is meaningful to humans and is recorded and transmitted by a medium. For example, the content may be a sentence, a movie, a television program, a music, a play, a photograph, a cartoon, an illustration, a computer graphic, an animation or the like.

In the above-described embodiment, the biological information includes the pulse wave, the brain wave, the change in the pupils and the like of the player. However, the biological information may include a blood pressure, a body temperature and the like of the player. Further, the biological information may be one of the pulse wave, the brain wave, the change in the pupils, the blood pressure and the body temperature of the player, or a combination thereof. For example, when the biological information is the brain wave alone, the psychological state of the player may be determined to any one of the "relaxed state", the "concentrated state", the "excited state" and the "bored state" by checking whether the brain wave is the alpha wave, the beta wave, the gamma wave, the theta wave or the like. In a case where the biological information is the pulse wave or the change in the pupils, the CPU 81 may determine that the sympathetic nerve is dominant when the biological information acquired by the biological information acquisition device 7 during the play of the game is equal to or greater than the base line. Further, in this case, the CPU 81 may determine that the parasympathetic nerve is dominant when the biological information is less than the base line.

In the above-described embodiment, the program executed by the CPU 81 is stored in the external storage medium or the like in advance, but the present invention is not limited thereto. For example, the program for executing the above-described processing may be applied to an existing general-purpose computer to function as the main body device 2 according to the above-described embodiment.

The method of providing such a program is arbitrary. For example, the program may be stored in a computer-readable recording medium (flexible disk, CD (Compact Disc)-ROM, DVD (Digital Versatile Disc)-ROM, etc.) and then distributed. Further, the program may be provided by storing the program in a storage on a network such as the Internet and downloading the program.

Further, in a case where the above-described processing is executed by cooperating between the OS (Operating System) and the application program or by sharing between the OS and the application program, only the application program may be stored in the recording medium or the storage. It is also possible to superimpose the program on a carrier wave and distribute it via a network. For example, the program may be posted on a Bulletin Board (BBS: Bulletin Board System) on the network, and the program may be distributed via the network. Then, the above-described processing may be executed by starting and executing the program in the same manner as another application program under the control of the OS.

It should be noted that the present invention allows various embodiments and modifications without departing from the broad spirit and scope of the present invention. The above-described embodiment is for explaining an example of the present invention, and is not intended to limit the scope of the present invention.

EXPLANATION OF REFERENCE NUMERALS

1: Game System
2: Main Body Device
3: Left Controller
4: Right Controller
5: Cradle
6: Stationary Monitor
7: Biological Information Acquisition Device
12: Display
13: Touch Panel
17: Left Terminal
21: Right Terminal
23: Slot
27: Lower Terminal
31: Upper Terminal
71: Pulse Wave Measurement Part
72: Brain Wave Measurement Part
73: Pupil Imaging Part
74: Processing Part
81: Cpu
82: Network Communication Part
83: Controller Communication Part
84: Flash Memory
85: Dram
86: Touch Panel Controller
91: Slot If

What is claimed is:

1. A content playback device comprising:

a biological information acquisition part for acquiring biological information of a user; and a control part for setting a psychological state corresponding to a situation of content during playback as a targeted psychological state, specifying a psychological state of the user from the biological information acquired by the biological information acquisition part, and changing a mode of the content during playback so that the psychological state specified from the biological information matches the targeted psychological state, wherein the control part does not change the mode of the content during playback when the psychological state specified from the biological information matches the targeted psychological state, when a brain wave of the user specified from the biological information acquired by the biological information acquisition part is a beta wave, the control part specifies that the psychological state of the user is a concentrated state, and when the brain wave is a gamma wave, the control part specifies that the psychological state of the user is an excited state, and wherein when the excited state continues for a predetermined period or longer, the control part specifies that the psychological state of the user is a fatigued state, and when the psychological state of the user is the fatigued state, the control part determines that it is impossible to immediately return the psychological state of the user to a state other than the fatigued state and instructs the user to interrupt the playback of the content, whereas when the psychological state is the concentrated state, the control part determines that it is possible to immediately return the psychological state of the user to a state other than the concentrated state and does not instruct the user to interrupt playback of the content.

2. The content playback device according to claim 1, wherein under the condition that the targeted psychological state is a state in which a sympathetic nerve is dominant, when the psychological state specified from the biological information is a state in which a parasympathetic nerve is dominant, the control part changes the mode of the content during playback so as to enhance the sympathetic nerve, and wherein under the condition that the targeted psychological state is a state in which the parasympathetic nerve is dominant, when the psychological state specified from the biological information is a state in which the sympathetic nerve is dominant, the control part changes the mode of the content during playback so as to suppress the sympathetic nerve.

3. The content playback device according to claim 1, wherein the control part sets a base line for determining which one of the sympathetic nerve and the parasympathetic nerve is dominant in the psychological state of the user based on the biological information acquired by the biological information acquisition part before the playback of the content.

4. The content playback device according to claim 3, wherein when the biological information acquired by the biological information acquisition part during the playback of the content is equal to or greater than the base line, the control part determines that the sympathetic nerve is dominant, and when the biological information is less than the base line, the control part determines that the parasympathetic nerve is dominant.

5. A content playback method comprising:

acquiring biological information of a user by a biological information acquisition part, and setting a psychological state corresponding to a situation of content during playback as a targeted psychological state, specifying a psychological state of the user from the biological information acquired by the biological information acquisition part, and changing a mode of the content during playback so that the psychological state specified from the biological information matches the targeted psychological state by a control part, wherein the control part does not change the mode of the content during playback when the psychological state specified from the biological information matches the targeted psychological state, when a brain wave of the user specified from the biological information acquired by the biological information acquisition part is a beta wave, specifying that the psychological state of the user is a concentrated state, and when the brain wave is a gamma wave, specifying that the psychological state of the user is an excited state, and when the excited state continues for a predetermined period or longer, specifying that the psychological state of the user is a fatigued state, and when the psychological state of the user is the fatigued state, determining that it is impossible to immediately return the psychological state of the user to a state other than the fatigued state and instructing the user to interrupt the playback of the content, whereas when the psychological state is the concentrated state, determining that it is possible to immediately return the psychological state of the user to a state other than the concentrated state and not instructing the user to interrupt playback of the content.

6. A program for causing a computer of a content playback device which comprises a biological information acquisition part for acquiring biological information of a user to execute a process for setting a psychological state corresponding to a situation of content during playback as a targeted psychological state, specifying a psychological state of the user from the biological information acquired by the biological information acquisition part, a process for changing a mode of the content during playback so that the psychological state specified from the biological information matches the targeted psychological state, and a process for not changing the mode of the content during playback when the psychological state specified from the biological information matches the targeted psychological state, a process for specifying that the psychological state of the user is a concentrated state when a brain wave of the user specified from the biological information is a beta wave, and specifying that the psychological state of the user is an excited state when a brain wave of the user specified from the biological information acquired by the biological information acquisition part is a gamma wave, a process for specifying that the psychological state of the user is a fatigued state when the excited state continues for a predetermined period or longer, and a process for determining that it is impossible to immediately return the psychological state of the user to a state other than the fatigued state and instructing the user to interrupt playback of the content when the psychological state of the user is the fatigued state, whereas determining that it is possible to immediately return the psychological state of the user to a state other than the concentrated state and not instructing the user to interrupt playback of the content when the psychological state is the concentrated state.

7. The content playback device according to claim 1, wherein when a brain wave of the user specified from the biological information acquired by the biological information acquisition part is an alpha wave, the control part specifies that the psychological state of the user is a relaxed state, and when the brain wave of the user is a theta wave, the control part specifies that the psychological state of the user is a bored state, and wherein under the condition that the targeted psychological state is the relaxed state, when the psychological state specified from the biological information is the bored state, the control part changes the mode of the content during playback such that the brain wave of the user becomes the alpha wave, wherein the control part does not change the mode of the content during playback when the psychological state specified from the biological information matches the targeted psychological state, when a brain wave of the user specified from the biological information acquired by the biological information acquisition part is a beta wave, specifies that the psychological state of the user is a concentrated state, and when the brain wave is a gamma wave, the control part specifies that the psychological state of the user is an excited state, and wherein when the excited state continues for a predetermined period or longer, the control part specifies that the psychological state of the user is a fatigued state, and when the psychological state of the user is the fatigued state, the control part determines that it is impossible to immediately return the psychological state of the user to a state other than the fatigued state and instructs the user to interrupt the playback of the content, whereas when the psychological state is the concentrated state, the control part determines that it is possible to immediately return the psychological state of the user to a state other than the concentrated state and does not instruct the user to interrupt playback of the content.

* * * * *